US 6,966,876 B2

(12) United States Patent
Irion et al.

(10) Patent No.: US 6,966,876 B2
(45) Date of Patent: Nov. 22, 2005

(54) DEVICE FOR HOLDING AND POSITIONING AN ENDOSCOPIC INSTRUMENT

(75) Inventors: Klaus M. Irion, Liptingen (DE); Ralph Boehm, Bodman-Ludwigshafen (DE)

(73) Assignee: Karl Storz GmbH & Co. KG, (DE)

( * ) Notice: Subject to any disclaimer, the term of this patent is extended or adjusted under 35 U.S.C. 154(b) by 255 days.

(21) Appl. No.: 10/428,383

(22) Filed: May 2, 2003

(65) Prior Publication Data

US 2003/0229338 A1 Dec. 11, 2003

Related U.S. Application Data

(63) Continuation of application No. PCT/EP01/12650, filed on Oct. 31, 2001.

(30) Foreign Application Priority Data

Nov. 3, 2000 (DE) .................................. 100 55 293

(51) Int. Cl.⁷ ................................................ A61B 1/00
(52) U.S. Cl. ........................ 600/102; 600/114; 600/227
(58) Field of Search ................................ 600/101–103, 600/114, 117, 118, 227–234; 606/130, 119, 606/1

(56) References Cited

U.S. PATENT DOCUMENTS

| | | | | |
|---|---|---|---|---|
| 2,697,433 A | 12/1954 | Zhender | ........................ | 128/83 |
| 3,308,675 A | 3/1967 | Jonsson | ........................ | 74/471 |
| 4,573,452 A | 3/1986 | Greenberg | ........................ | 128/20 |
| 5,184,601 A | 2/1993 | Putman | ........................ | 128/4 |
| 5,201,742 A | 4/1993 | Hasson | ........................ | 606/130 |
| 5,284,129 A * | 2/1994 | Agbodoe et al. | ........................ | 600/230 |
| 5,330,485 A | 7/1994 | Clayman et al. | ........................ | 606/130 |
| 5,766,126 A | 6/1998 | Anderson | ........................ | 600/102 |
| 5,767,839 A | 6/1998 | Rosenberg | ........................ | 345/161 |
| 5,810,712 A | 9/1998 | Dunn | ........................ | 600/114 |
| 5,891,158 A * | 4/1999 | Manwaring et al. | ........................ | 606/130 |

FOREIGN PATENT DOCUMENTS

| | | |
|---|---|---|
| DE | 94 15 039 | 9/1994 |
| DE | 196 47 516 A1 | 5/1998 |
| DE | 100 55 293 A1 | 5/2002 |

* cited by examiner

Primary Examiner—Beverly M. Flanagan
(74) Attorney, Agent, or Firm—St. Onge Steward Johnston & Reens LLC

(57) ABSTRACT

A device for holding and positioning an endoscopic instrument introduced through a body surface of a patient has a holder for the instrument, which holder is designed in such a way that the instrument can be positioned relative to the body surface in different spatial tilt positions. The holder has a first bow-shaped element whose two end portions are arranged directed towards the body surface, and whose middle portion is directed away from the body surface, the first bow-shaped element being pivotable about a first pivot axis which extends through both end portions. The holder has a second bow-shaped element whose end portions are directed towards the body surface, but arranged offset by approximately 90° relative to the end portions of the first bow-shaped element, and whose middle portion is directed away from the body surface by substantially the same distance as the first bow-shaped element, the second bow-shaped element being pivotable about a second pivot axis which extends through both end portions of the second bow-shaped element, and both bow-shaped elements each having an opening which extends along said elements, and an overlapping region of the openings serving as a guide for the instrument.

25 Claims, 5 Drawing Sheets

DEVICE FOR HOLDING AND POSITIONING AN ENDOSCOPIC INSTRUMENT

CROSS REFERENCE TO PENDING APPLICATIONS

The present application is a continuation of pending International Patent Application PCT/EP01/12650 filed on Oct. 31, 2001 which designates the United States, and which claims priority of German Patent Application DE 100 55 293.5 filed on Nov. 3, 2000.

BACKGROUND OF THE INVENTION

The invention relates to a device for holding and positioning an endoscopic instrument introduced through a body surface of a patient, with a holder for the instrument, which holder is designed in such a way that the instrument can be positioned relative to the body surface in different spatial tilt positions, which holder has a first bow-shaped element whose two end portions are arranged directed towards the body surface, and whose middle portion is directed away from the body surface, and which holder has a second bow-shaped element whose end portions are directed towards the body surface, but arranged offset by approximately 90° relative to the end portions of the first bow-shaped element, and whose middle portion is directed away from the body surface by substantially the same distance as the first bow-shaped element, and the instrument being guided at an overlapping region of the two bow-shaped elements.

A device of this kind is known from the document DE 94 15 039 U1.

A device of this kind is used in the context of minimally invasive surgery. In minimally invasive surgery, an instrument, which in the context of the present invention is understood as a working instrument such as scissors or forceps for tissue preparation and also as an endoscope, is introduced into the operating site via an incision in the body surface, in order to perform a surgical intervention under endoscopic visual control. The instrument is in this case usually introduced into the inside of the body via a trocar which is fitted into the incision.

Particularly if the instrument is an endoscope, it is sometimes necessary to position the endoscope in different tilt positions relative to the body surface in order to be able to inspect all areas of the operating site.

The positioning of the instrument or trocar has customarily been carried out by assistants. However, it would be desirable for simple manoeuvres such as positioning of the instrument to be taken over by a controllable holding and positioning device, which would mean less assistance was required and, in addition, would permit more exact positioning of the instrument.

Thus, it would be sensible if the endoscope, which carries the camera for video image recording, were to be held and guided via an endoscope holder and guidance system. Holding and positioning of an endoscope or instrument is possible, for example, with a device known from U.S. Pat. No. 4,573,452. This device has a selectively tensionable cable-type component which is released in order to move the endoscope, after which the endoscope can be brought manually into the desired position, and is then clamped to a rigid structure in order to fix the endoscope in the set position. A disadvantage of this known device is that the positioning, i.e. the changing of the position, of the endoscope can only be done manually.

Another manually adjustable holding and positioning system is known from U.S. Pat. No. 5,810,712 and has a holder in the form of a ring, with a ball mounted in the latter via a cardanic suspension and acting as a seat for the instrument. The ball of the cardanic suspension can be fixed in the desired tilt position.

However, motor-driven devices for holding and positioning of an instrument are also already known, for example from U.S. Pat. No. 5,184,601 or from U.S. Pat. No. 5,766,126. These devices not only make it possible to receive the endoscope and fix it in position, but also permit intracorporeal adjustment, during the operation, of the working instruments being used in said operation, either by direct control from outside or automatically by detection of the instrument tips in the image processing and by corresponding control of the guidance system, or by detection of the position and direction of the instruments via position sensors and by corresponding control of the holding and positioning device.

A disadvantage of these intelligent holding and positioning devices, however, is their complicated structure and in particular their overall size, which conceals a large area of the operating site. Moreover, these known devices are awkward to install and can only be cleaned with some difficulty. Because of their complicated structure and the use of sensitive components, these devices cannot be sterilized in an autoclave and, for hygiene purposes, they therefore need to be provided with a sterile foil cover during the operation. Moreover, these devices are expensive and, because of their heavy and solid design, they are generally not transportable, so that they cannot be used successively at different locations.

Because of these disadvantages, these known devices are not suitable for simple and brief minimally invasive procedures, because the installation and preparation times for these known devices are out of all proportion with the time needed for the operation.

The document DE 94 15 039 U1 mentioned at the outset describes a device for guiding surgical instruments, for example a trocar, where the two bow-shaped elements, at their two end portions, can be moved via rollers along a respective guide track shaped as a segment of a circle. This device, which is comparatively simple from the point of view of its construction, means that the instrument clamped with its shaft in the device is permitted the area of movement of a rectangular double pyramid whose tips pointing towards each other coincide at an invariant point lying on the shaft axis of the instrument, and both ends of the shaft move on a respective spherical sector surface, the centre points of these lying at the invariant point. However, guiding the two bow-shaped elements on curved guide tracks via rollers has various disadvantages.

Because of the curvature of the guide tracks, the frame of this device has a considerable overall height, which has the disadvantage that the invariant point of the instrument's movement lays far above the body surface. Moreover, it is difficult to provide the rollers with a motor drive if this is desired for automation of the instrument's positioning. Moreover, because of the guide rollers and guide tracks, this known device has a great many nooks and crannies in which it is possible for dirt to accumulate, which can be removed only with difficulty. Moreover, in this known device, it is necessary, because of the guide tracks, for the frame to be made rectangular, which requires a greater amount of space.

Furthermore, U.S. Pat. No. 5,330,485 discloses an instrument guidance device used for guiding instruments in brain surgery. This known device has two differently curved bow-shaped elements which are secured on a common pivot axis and can be pivoted about the latter. In this device, the instrument to be guided cannot be moved about an invariant point.

The object of the invention therefore is to make available a device, of the type mentioned in the introduction, which has an even simpler structure, can be set up quickly, and takes up the least possible space on the patient's body.

SUMMARY OF THE INVENTION

According to the invention, a device for holding and positioning an endoscopic instrument introduced through a body surface of a patient is provided, comprising a holder for said instrument, said holder being designed in such a way that said instrument can be positioned relative to said body surface in different spatial tilt positions, said holder having a first bow-shaped element having two end portions arranged directed towards said body surface, and having a middle portion directed away from said body surface, said first bow-shaped element being pivotable about a first pivot axis extending through both end portions of said first bow-shaped element, said holder having a second bow-shaped element having end portions directed towards said body surface, but arranged offset by approximately 90° relative to said end portions of said first bow-shaped element, and having a middle portion directed away from said body surface by substantially the same distance as said first bow-shaped element, said second bow-shaped element being pivotable about a second pivot axis extending through both end portions of said second bow-shaped element, and said instrument being guided at an overlapping region of said two bow-shaped elements.

Accordingly, in the device according to the invention, the holder for the instrument is formed by two bow-shaped elements which are arranged with one crossing over the other and which, because of their pivotability about the first and second pivot axes, act as a cardanic suspension for the instrument. The structure of the device according to the invention is particularly simple because the cardanic suspension of the instrument requires only the two pivotable bow-shaped elements. The device according to the invention permits manual positioning, as in the known systems, but it is also suitable for a positioning controlled by motor drives, for example with the bow-shaped elements being pivoted by means of motor drives which receive their control signals from a corresponding control unit. The device according to the invention is also easy to set up, because it can be placed directly on the body surface around the incision. Since the holder is basically formed only by the two bow-shaped elements, the operating site is not concealed to any great extent either. The device according to the invention is also easy to clean, and, with a suitable choice of material for the bow-shaped elements, it can also be autoclaved. Changing the instrument can be done easily, because the instrument to be inserted into the device simply has to be arranged at the overlap of the two bow-shaped elements. By designing the holder in the form of two bow-shaped elements which are offset approximately 90° to one another, it is possible to obtain any desired tilt positions relative to the body surface.

Arranging the instrument at the overlap area of the bow-shaped elements is particularly easy if, according to a preferred embodiment, both bow-shaped elements have an opening which extends along the elements, and the overlap region of the two openings serves as a guide or passage for the instrument, because the instrument can then be easily introduced into the overlap region of the openings.

In a preferred embodiment, the first pivot axis and the second pivot axis are situated in immediate proximity to the body surface.

When an instrument, for example an endoscope or a trocar, is introduced into the inside of the body via an incision, the pivot point of the instrument, in respect of the tilt positions relative to the body surface, lies approximately in the incision. The aforementioned measure now ensures that, even when using the device according to the invention, this "natural" pivot point of the instrument within the incision is almost fully maintained, said pivot point being formed in the cardanic suspension by the point of intersection of the two pivot axes.

In order to bring this so-called invariant point of the cardanic suspension even completely into the incision, a further preferred embodiment comprises means for lifting the body surface into the space spanned by the bow-shaped elements.

These means can be of a mechanical type, for example a mechanical leverage system comprising a gripper or tissue hook which engages, through the incision, under the body surface and lifts the body surface, or said means can consist of an under pressure applied to the body surface from the outside for lifting said body surface and thus for bringing the invariant point of the pivot movement into the incision.

In a further preferred embodiment, the bow-shaped elements are designed as curved flat bars.

This measure affords the advantage that the device according to the invention does not to any great extent conceal or obstruct the operating site.

In a further preferred embodiment, the bow-shaped elements are secured with their end portions on an annular base element which can be placed on the body surface, the pivot axes lying in the base element.

Because of the base element, the device according to the invention can be positioned on the body surface around the incision as a compact and easy-to-handle unit, the base element advantageously ensuring that the device according to the invention bears on the body surface substantially free from any undesired tilting.

In this connection, it is preferable for the base element to be heavier than the bow-shaped elements.

By means of this measure, the centre of gravity of the device according to the invention is advantageously brought as close as possible to the body surface, as a result of which the device according to the invention is particularly stable against tilting forces and tilting moments which act on the device and are caused by the weight and the angle position of the instrument.

To further stabilize the device according to the invention against the aforementioned tilting forces and tilting moments, provision is made, in a further preferred embodiment, for the base element to be able to be secured to the body surface.

In preferred embodiments, the securing of the base element to the body surface can be done adhesively, for example using a two-sided adhesive tape, or, as is indicated in a still further preferred embodiment, by applying a vacuum via which the base element is sucked onto the body surface.

In a further preferred embodiment, the base element is connected to a fixed support frame.

This measure can advantageously compensate for any disturbance movements of the abdominal wall, caused for example by breathing, and can likewise take up forces caused by the weight and angle position of the instrument in order to fix the device in a fixed position on the body surface.

In a further preferred embodiment, the bow-shaped elements are designed approximately in the shape of a semicircle, and the openings extend along almost the entire length of the bow-shaped elements.

This measure has the advantage that the instrument can be positioned, with the device according to the invention, in virtually the entire spatial angle range from +90° to −90° about both pivot axes in relation to the vertical. In other words, in this embodiment all the pivot angles in the half-space above the body surface are covered.

In practice, it is preferred if the tilting of the bow-shaped elements can be limited to less than ±90°, preferably to ±70°, relative to the vertical.

Such limiting of the pivot ranges of the two bow-shaped elements can be achieved by mechanical means or, in the case of motorized control of the pivoting of the bow-shaped elements, via a corresponding switching-off of the motor drives when the limit angle is reached.

In a further preferred embodiment, a motor drive is provided for both bow-shaped elements in order to pivot said bow-shaped elements about the first and second pivot axes.

As has already been mentioned, the device according to the invention is not just suitable for manual positioning of the instrument, but instead it is also possible for motor drives to be arranged in a suitable manner on the bow-shaped elements in order to effect a controlled positioning of the instrument. A controlled motor actuation of the bow-shaped elements has the advantage that no assistants are needed and the positioning can be more finely tuned, and that the pivoting of the instrument can take place on the basis of signals, for example from position sensors which monitor the position of the instrument tip.

In this sense it is preferred if the motor drives each have position detectors, so that a fully automatic control of the cardanic suspension of the instrument is obtained.

In a further preferred embodiment, the motor drives are arranged inside the space spanned by the bow-shaped elements.

This affords the advantage of a still more compact construction, and electrical components outside the spatial structure spanned by the bow-shaped elements can be avoided.

In a further preferred embodiment, the holder is designed in such a way that the instrument is rotatable about its longitudinal axis in the guide of the bow-shaped elements and/or is displaceable in the direction of its longitudinal axis.

This measure has the advantage that, in addition to the two degrees of freedom about the two pivot axes, provided for by the cardanic suspension via the two bow-shaped elements, the instrument has two further, preferably controllable, degrees of freedom of its positioning, as a result of which a still more precise positioning of the instrument is made possible. If the instrument is an endoscope, moving the instrument forward and backward can produce an enlargement or reduction of the viewing field in the nature of a zoom effect, or the point of view can be changed. By turning the endoscope about its longitudinal axis, the image of the operating site displayed on the video screen can be correctly oriented. If the endoscope has a viewing angle oblique with respect to its longitudinal axis, turning the endoscope about its longitudinal axis can vary the image section.

In this connection, it is preferred if at least one motor drive is arranged on the holder for the rotatability of the instrument about the longitudinal axis and/or for the displaceability of the instrument in the direction of the longitudinal axis.

With this measure, the two aforementioned degrees of freedom of movement of the instrument can also be controlled by computer instead of manually.

It is further preferred if the at least one motor drive for the rotation of the instrument and/or for the displacement of the instrument acts indirectly on the instrument.

This has the advantage of avoiding the sterility and sealing problems which possibly arise if the motor drives act directly on the instrument. In this sense, the at least one motor drive can act indirectly on the instrument by way of a magnetic coupling.

In a further preferred embodiment, the motor drives are designed as step motors.

It is of advantage here that the desired position can be taken up in a reproducible manner. In connection with the provision of position detectors, for example in the form of angle encoders, the actual position of the instrument can be detected, stored, and then taken up again reproducibly.

In a further preferred embodiment, a safety switch-off is provided for the motor drives so that, by means of a measurement voltage induced in the instrument upon contact of the instrument with tissue inside the body, a measurement current flows which switches off the motor drives.

This measure to a great extent satisfies the requirements to be placed on the safety of the device according to the invention in order to avoid undesirable collision of the instrument with uninvolved tissue and to avoid injuries caused by this.

In a further preferred embodiment, the device according to the invention has a control unit for continuously determining the positions of the instruments and for controlling the motor drives.

By means of this measure, the instrument received in the device can be positioned under electronic control. The positioning can be entered interactively, for example, by joysticks or speech input, or using the direction information of a fully automatic tracking of the working instruments via special real-time image processing.

A further device which is suitable as a holding and positioning device for an instrument is disclosed in the two German patent applications filed on the same day for the same Applicant and with the title "Simulationsvorrichtung mit zumindest zwei Bewegungsfreiheitsgraden für ein Instrument" [Simulation device with at least two degrees of freedom of movement for an instrument], the disclosure of which two applications is incorporated expressly herein by reference.

In a modification of the simulation device described there, it is preferable if the ball-shaped element forming part of the cardanic suspension of that device is omitted. The double bevel-wheel gear described there for the degrees of freedom of movement of the instrument about and in the longitudinal direction of the instrument can also be provided in the present device.

Further features and advantages will become evident from the following description and from the attached drawing.

It will be appreciated that the features mentioned above, and the features still to be explained below, can be used not only in the respectively stated combination, but also in other combinations or in isolation, without departing from the scope of the present invention.

BRIEF DESCRIPTION OF THE DRAWINGS

An illustrative embodiment of the invention is shown in the drawing and is explained in greater detail in the description below.

DETAILED DESCRIPTION OF A PREFERRED EMBODIMENT

Figure 1:
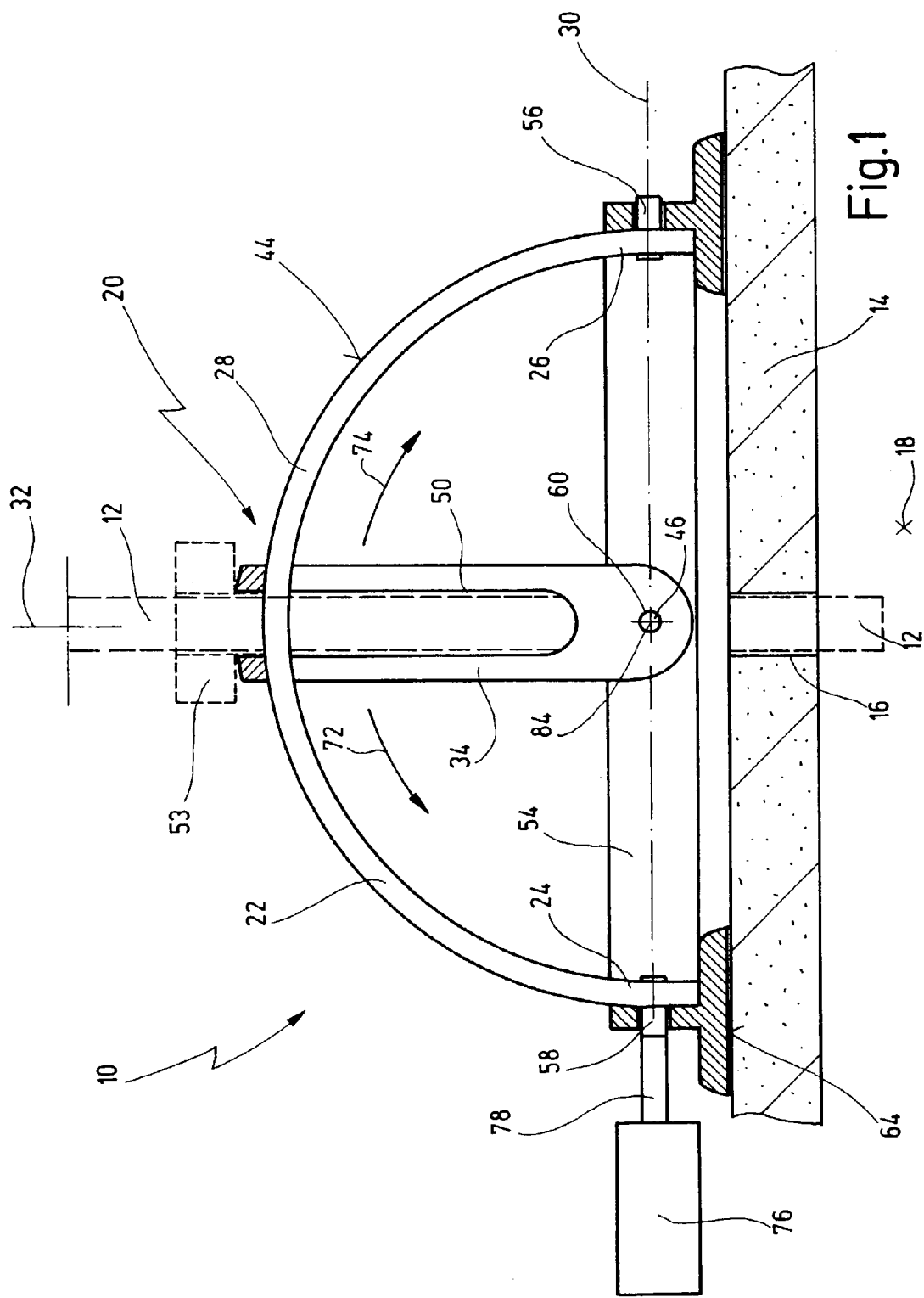
FIG. 1 shows a device for holding and positioning an instrument, in a partially cut-away first side view.
Figure 2:
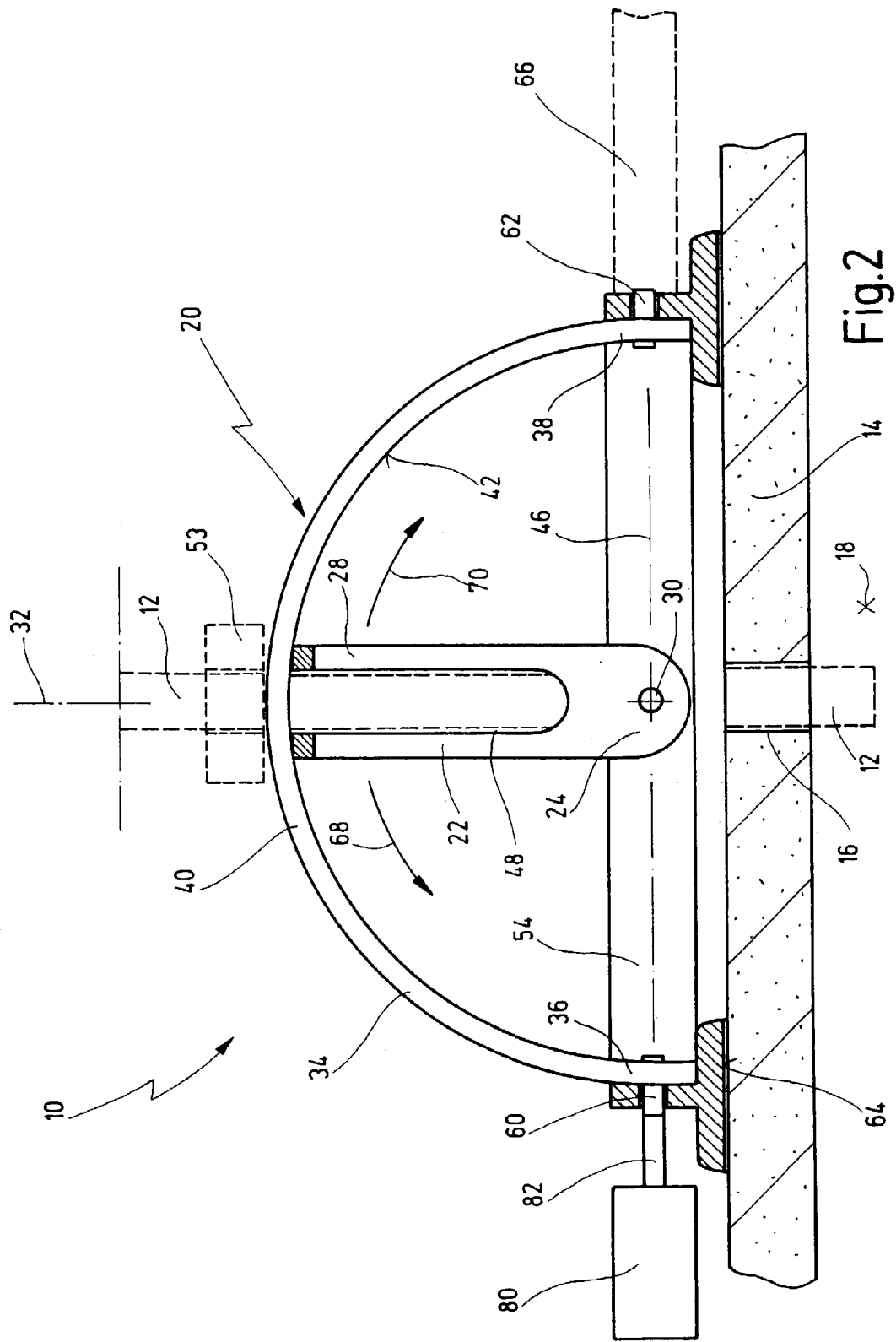
FIG. 2 shows the device from FIG. 1 in a partially cut-away side view turned 90° in relation to FIG. 1.
Figure 3:
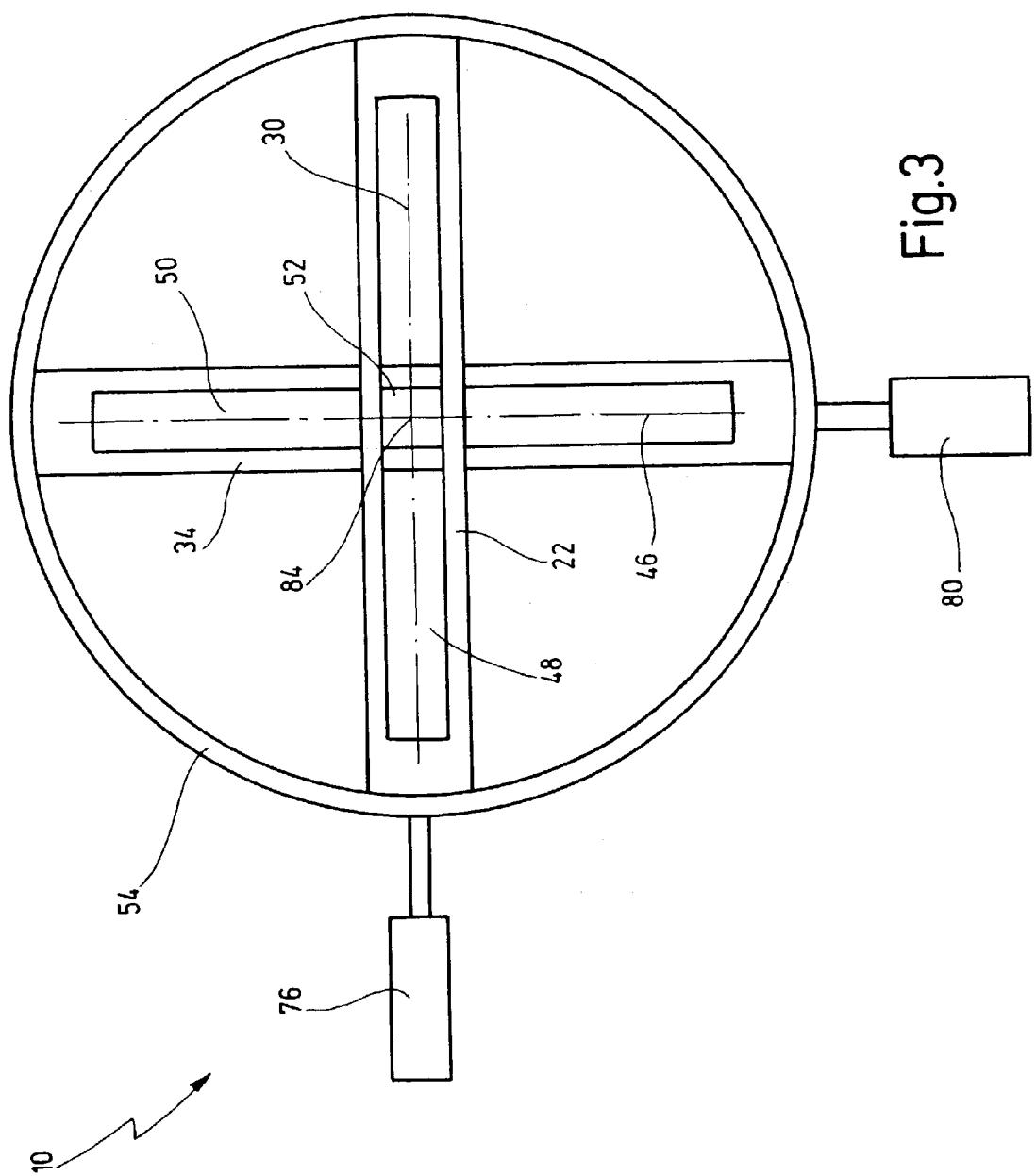
FIG. 3 shows the device from FIGS. 1 and 2 in a plan view in which, compared to FIG. 1, some parts have been omitted.
Figure 4:
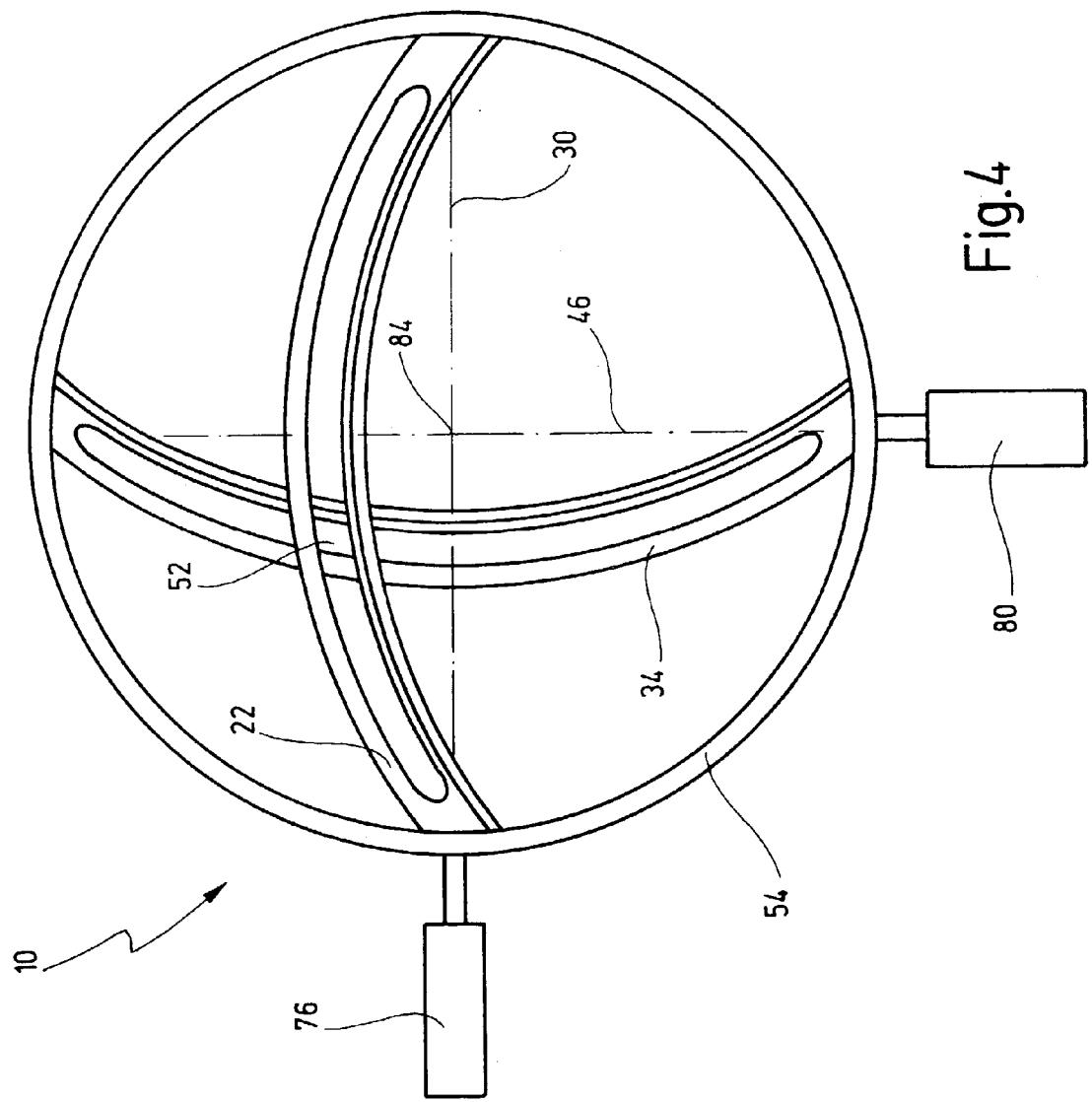
FIG. 4 shows another plan view of the device from FIGS. 1 to 3 in an operating position which has changed compared to FIGS. 1 to 3.
Figure 5:
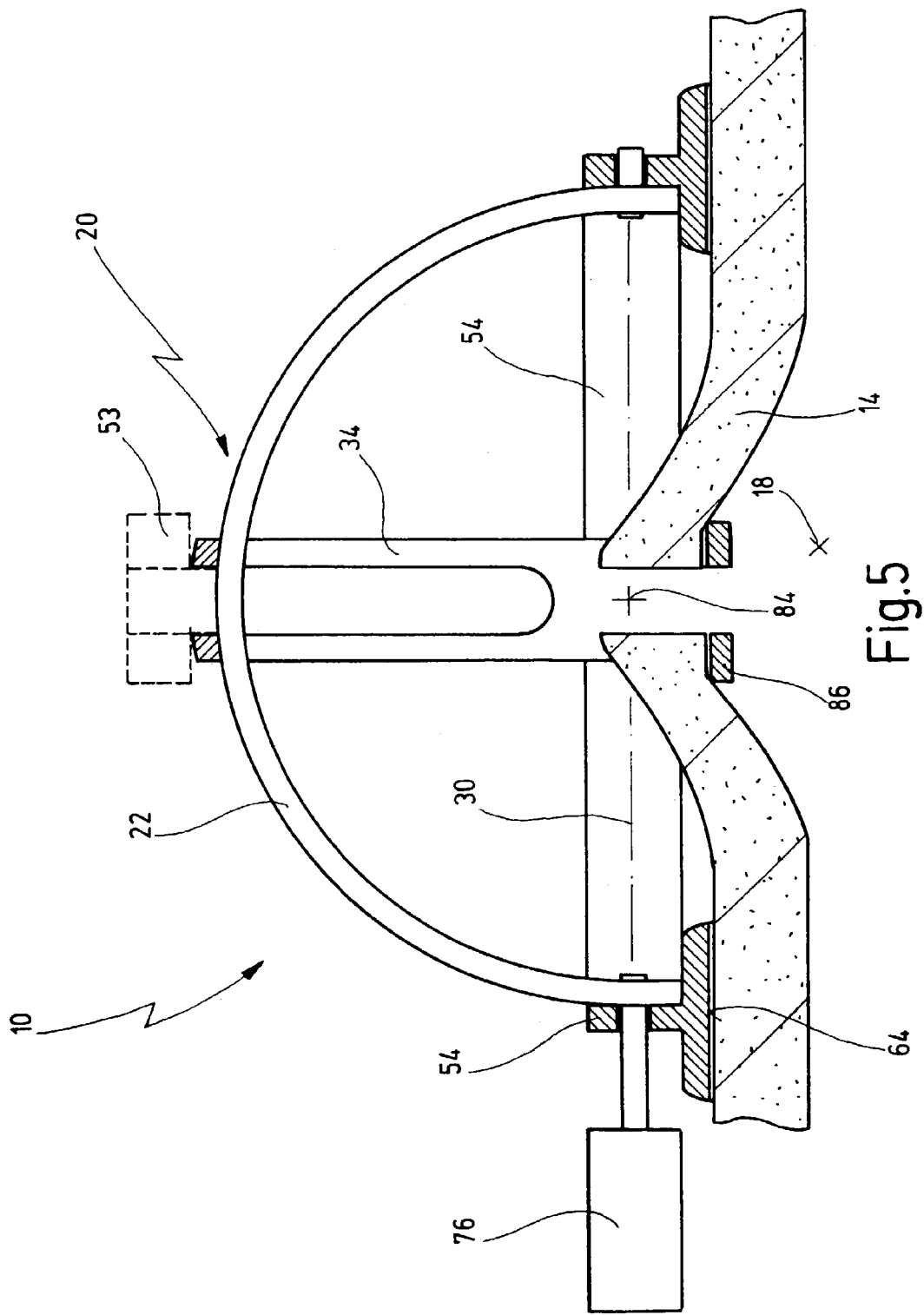
FIG. 5 shows the device from FIGS. 1 to 4, with a further aspect of the invention.

FIGS. 1 to 5 show a device, provided with general reference number 10, for holding and positioning an instrument 12 (FIGS. 1, 2 and 5).

The instrument 12 is introduced through a body surface 14, for example through the abdominal wall, via an incision 16 in the body surface 14 and into the inside 18 of the body of a patient. The device 10 is being used for holding and positioning the instrument 12 in the context of a minimally invasive procedure.

The instrument 12 is an endoscopic instrument, for example an endoscope itself, or a working instrument, for example scissors, forceps or the like, and the instrument 12 can if appropriate be introduced through a trocar into the inside 18 of the body, and the trocar is then correspondingly held and positioned by the device 10, while the instrument 12 is then guided through the trocar.

The device 10 has a holder 20 for the instrument 12, which holder 20 is designed in such a way that the instrument 12 can be positioned in various spatial tilt positions relative to the body surface 14.

For this purpose, the holder 20 has a first bow-shaped element 22 which has two end portions 24 and 26. The two end portions 24 and 26 are arranged directed towards the body surface 14.

A middle portion 28 between the end portions 24 and 26 of the first bow-shaped element 22 is directed away from the body surface 14, i.e. farther away from the latter than are the end portions 24 and 26.

The first bow-shaped element 22 is pivotable about a first pivot axis 30 which extends through both end portions 24 and 26.

The holder 20 also has a second bow-shaped element 34 which has two end portions 36 and 38. The end portions 36 and 38 are directed towards the body surface 14. The end portions 36 and 38 are offset approximately 90° in relation to the end portions 24 and 26 of the first bow-shaped element 22.

A middle portion 40 of the second bow-shaped element 34 between the end portions 36 and 38 is directed away from the body surface 14, i.e. farther away from the body surface 14 than are the end portions 36 and 38.

The middle portion 40 of the second bow-shaped element 34 rises substantially the same distance from the body surface 14 as the middle portion 28 of the first bow-shaped element 22. To be more precise, an inside 42 of the second bow-shaped element 34 is at the same distance from the body surface 14 as an outside 44 of the first bow-shaped element 22, so that the inside 42 and the outside 44 lightly touch.

The second bow-shaped element 34 is pivotable about a second pivot axis 46 which extends through both end portions 36 and 38. The second pivot axis 46 accordingly extends approximately at right angles to the first pivot axis 30.

The first bow-shaped element 22 has an opening 48 in the form of an oblong hole which extends along the first bow-shaped element 22, more precisely along the middle portion 28.

The second bow-shaped element 34 has an opening 50 which is likewise designed as an oblong hole and which extends along the second bow-shaped element 34.

An overlap region 52 of the two openings 50 and 48 (see FIG. 3) serves as a guide for the instrument 12, i.e. the instrument 12 is received in the guide. In FIGS. 3 and 4, the instrument 12 has been omitted for the sake of clarity.

The first bow-shaped element 22 and the second bow-shaped element 34 are designed as curved flat bars, and they are of approximately semicircular design in the illustrative embodiment shown. The radius of the outside 44 of the first bow-shaped element 22 corresponds to the radius of the inside 42 of the second bow-shaped element 34. The openings 48 and 50 extend almost the entire length of the bow-shaped elements 22 and 34.

The instrument 12 is guided by means of an inset 53 in the passage formed by the overlap region 52 and can, if appropriate, be fixed therein.

Both bow-shaped elements 22 and 34 are secured on an annular base element 54. The base element 54 has an approximately round shape. The pivot axes 30 and 46 extend through the base element 54. For this purpose, the first bow-shaped element 22 is, in the simplest case, connected to the base element via axle pins 56 and 58. Correspondingly, the second bow-shaped element 34 is connected pivotably to the base element 54 via axle pins 60 and 62.

When using the device 10, it is placed with the base element 54 onto the body surface 14. To achieve a wider and more tilt-stable bearing, the base element 54 has a widened bearing surface 64 directed towards the body surface 14, which widened bearing surface 64 extends completely or partially around the circumference of the base element 54. In FIGS. 3 and 4, the widened bearing surface 64 is not shown.

As regards the weight distribution of the device 10, it is useful, particularly because of the tilt moments caused by the inserted instrument 12 and its oblique setting, if the centre of gravity lies as close as possible to the body surface 14, for which purpose the base element 54 as a whole has a greater weight than the bow-shaped elements 22 and 34.

In addition, the base element 54 can be secured to the body surface 14, for example adhesively using a two-sided adhesive tape which is attached on the one hand to the bearing surface 64 and on the other hand to the body surface 14, or by applying a vacuum to the bearing surface 64, by which means the bearing surface 64 and thus the base element 54 are sucked onto the body surface 14.

To further stabilize the device 10 on the body surface 14, the base element 54 is connected to a support arm of a positionally fixed support frame 66. For example, the support system shown in FIGS. 2 and 3 of DE 199 02 036 C1, to which reference is here made, is suitable as such a support frame 66.

The holder 20 of the device 10 permits a movement of the instrument 12, with respect to the degrees of freedom of pivot movements, about the first pivot axis 30 in the direction of arrows 68 and 70 in FIG. 2 and about the second pivot axis 46 in the direction of arrows 72 and 74. Because of the cardanic suspension formed by the bow-shaped elements 22 and 34, the instrument 12 can accordingly assume tilt positions relative to the body surface 14 and to the vertical 32 at any desired solid angles in the space above the body surface 14. FIG. 4 shows, by way of example, a tilt position of the bow-shaped elements 22 and 34 in which both the bow-shaped element 22 and also the bow-shaped element 34 are tilted away from their vertical position shown in FIGS. 1 to 3.

While the bow-shaped elements 22 and 34 are in principle pivotable relative to the pivot axes 30 and 46 in an angle range of −90° to +90°, provision can be made to limit the pivot range of the instrument 12 relative to both pivot axes to ±70° in order to avoid extreme oblique settings of the instrument 12. This can be achieved using mechanical limits to the pivotability of the bow-shaped elements 22 and 34, for example by the openings 48 and 50 extending less close to the end portions 24, 26 and 36, 38, respectively.

For the pivoting of the first bow-shaped element 22, a motor drive 76 is provided which with its output shaft 78 acts on the axle 58 in order to pivot the bow-shaped element 22 about the first pivot axis 30. Correspondingly, in order to pivot the second bow-shaped element 34, a motor drive 80 is provided which with its output shaft 82 acts on the axle 60 in order to pivot the second bow-shaped element 34 about the second pivot axis 46.

The motor drives 76 and 80 each have position detectors, for example in the form of angle encoders, in order to detect the respective current position of the bow-shaped elements 22 and 34 relative to the pivot axes 30 and 46. The motor drives 76 and 80 are designed as step motors. A control unit (not shown) is also provided for continuously determining the position of the instrument 12 and for controlling the motor drives 76 and 80.

While the motor drives 76 and 80 in FIGS. 1 to 5 are arranged outside the space spanned by the bow-shaped elements 22 and 34, the motor drives 76 and 80 can also be arranged inside this space in order to obtain a still more compact construction.

Instead of arranging the motor drives 76 and 80 in axial continuation of the axles 58 and 60, respectively, the motor drives 76 and 80 can also, for example, be arranged protruding vertically upwards, in which case the output shafts 78 and 82, respectively, act on the axles 58 and 60 via a bevel-wheel gear. This arrangement can be of advantage if, in an arrangement as is provided in FIGS. 1 to 5, the dimensions of the motor drives 76 and 80 would make it impossible or difficult to arrange the base element 54 and thus the pivot axes 30 and 46 near enough to the body surface 14.

In the device 10, the first pivot axis 30 and the second pivot axis 46 are already situated in immediate proximity to the body surface 14, this proximity being substantially closer than the distance to be inferred from the drawing.

A point of intersection 84 of the first pivot axis 30 with the second pivot axis 46 defines the invariant point of the cardanic suspension formed by the bow-shaped elements 22 and 34, i.e. when the instrument 12 tilts about the first axis 30 and the second axis 46, said instrument 12 tilts about the point of intersection 84 as pivot point. Since, however, the instrument 12 is also guided in the incision 16, it is important to bring the point of intersection 84 as close as possible to or into the incision 16.

According to FIG. 5, the device 10 is accordingly provided with means 86 for lifting the body surface 14 into the space spanned by the bow-shaped elements 22 and 34 so that the incision 16 is brought into the point of intersection 84 of the two pivot axes 30 and 46.

The means 86 for lifting the body surface 14 in FIG. 5 are designed in the form of a mechanical leverage system, which for example is in the form of two grippers which are guided through the incision 16 and grip under the body surface 14 and pull the latter into the space spanned by the bow-shaped elements 22 and 34.

Instead of a mechanical leverage system, however, underpressure acting on the body surface 14 from the outside can also be applied as a means of lifting the body surface 14.

In a manner which is not illustrated, the holder 20 is moreover designed in such a way that the instrument 12 in the guide, formed by the overlap region 52, is rotatable about its longitudinal axis and/or displaceable in the direction of its longitudinal axis. In this way, in addition to the two degrees of freedom of the pivoting movement about the pivot axes 30 and 46, the instrument 12 is permitted two further, preferably controlled, degrees of freedom of movement.

For said two additional degrees of freedom too, motor drives are preferably arranged on the holder 20 which are likewise equipped with position detectors in order to determine the current position of the instrument 12 in relation to these degrees of freedom and, via the already mentioned control unit, to control the position of the instrument 12.

Regarding the motor drives (not shown) for the rotation of the instrument or movement of the instrument 12, it is preferable for these motor drives to act on the instrument 12 indirectly, for example by means of a magnetic coupling.

Furthermore, for all the aforementioned motor drives, a safety switch-off is provided so that, by means of a measurement voltage induced in the instrument 12 when said instrument 12 makes contact with tissue in the inside 18 of the body, a measurement current flows which switches off the motor drives 76, 80 and the further motor drives for the rotatabilty and displaceability of the instrument.

Furthermore, the motor drives 76 and 80 can be equipped with a cut-off switch so that the tilt range of the instrument 12 about the pivot axes 30 and 46 can be limited by motor control instead of by mechanical measures.

What is claimed is:

1. A device for holding and positioning an endoscopic instrument introduced through a body surface of a patient, comprising:

a holder for said instrument, said holder being designed in such a way that said instrument can be positioned relative to said body surface in different spatial tilt positions, said holder having a first bow-shaped element having two end portions arranged directed towards said body surface, and having a middle portion directed away from said body surface, said first bow-shaped element being pivotable about a first pivot axis extending through both end portions of said first bow-shaped element, said holder having a second bow-shaped element having end portions directed towards said body surface, but arranged offset by approximately 90° relative to said end portions of said first bow-shaped element, and having a middle portion directed away from said body surface by substantially the same distance as said first bow-shaped element, said second bow-shaped element being pivotable about a second pivot axis extending through both end portions of said second bow-shaped element, and said instrument being guided at an overlapping region of said first-bow-shaped element and said second bow-shaped element.

2. The device of claim 1, wherein said first pivot axis and said second pivot axis are situated in immediate proximity to said body surface.

3. The device of claim 1, wherein said first bow-shaped element and said second bow-shaped element are designed as curved flat bars.

4. The device of claim 1, wherein said first bow-shaped element and said second bow-shaped element are secured with their end portions on an annular base element which can be placed on said body surface, said first pivot axis and second pivot axis lying in said base element.

5. The device of claim 4, wherein said base element is heavier than said first bow-shaped element and said second bow-shaped element.

6. The device of claim 1, wherein said first bow-shaped element and said second bow-shaped element are secured with their end portions on an annular base element which can be placed on said body surface, said first pivot axis and said second pivot axis lying in said base element, and wherein said base element can be secured to said body surface.

7. The device of claim 6, wherein said base element can be adhesively secured to said body surface.

8. The device of claim 1, wherein said first bow-shaped element and said second bow-shaped element are secured with their end portions on an annular base element which can be placed on said body surface, said first pivot axis and second pivot axis lying in said base element, and wherein said base element can be secured to said body surface by suctioning said base element onto said body surface by applying a vacuum.

9. The device of claim 1, wherein said first bow-shaped element and said second bow-shaped element are secured with their end portions on an annular base element which can be placed on said body surface, said first pivot axis and second pivot axis lying in said base element, and wherein said base element is connected to a fixed support frame.

10. The device of claim 1, wherein said first bow-shaped element has a first opening and said second bow-shaped element has a second opening wherein said first opening and said second opening form an overlap region of said first opening and second opening such that said overlap region serves as a guide or passage for said instrument.

11. The device of claim 10, wherein said first bow-shaped element and said second bow-shaped element are designed approximately in the shape of a semicircle, and said first opening and said second opening extend along almost the entire length of said first bow-shaped element and said second bow-shaped element.

12. The device of claim 1, wherein a tilting angle of said first bow-shaped element and said second bow-shaped element can be limited to less than ±90° relative to the vertical.

13. The device of claim 1, wherein a motor drive is provided for said first bow-shaped element and said second bow-shaped element in order to pivot said first bow-shaped element and said second bow-shaped element about said first pivot axis and said second pivot axis.

14. The device of claim 13, wherein said motor drive has position detectors.

15. The device of claim 1, wherein a motor drive is provided for said first bow-shaped element and said second bow-shaped element in order to pivot said first bow-shaped element and said second bow-shaped element about said first pivot axis and second pivot axis, and wherein said motor drive is arranged inside the space spanned by said first bow-shaped element and said second bow-shaped element.

16. The device of claim 1, wherein said holder is designed in such a way that said instrument is rotatable about its longitudinal axis in the guide of said first bow-shaped element and said second bow-shaped element.

17. The device of claim 16, wherein at least one motor drive is arranged on said holder for rotatability of said instrument about said longitudinal axis.

18. The device of claim 17, wherein said at least one motor drive for rotation of said instrument acts indirectly on said instrument.

19. The device of claim 1, wherein said holder is designed in such a way that said instrument is displaceable in direction of its longitudinal axis.

20. The device of claim 19, wherein at least one motor drive is arranged on said holder for said displaceability of said instrument in direction of said longitudinal axis.

21. The device of claim 20, wherein said at least one motor drive for displacement of said instrument acts indirectly on said instrument.

22. The device of claim 1, wherein a motor drive is provided for said bow-shaped elements in order to pivot said bow-shaped elements about said first and second pivot axes, and wherein said motor drives are designed as step motors.

23. The device of claim 1, wherein a motor drive is provided for said first bow-shaped element and said second bow-shaped element in order to pivot said first bow-shaped element and said second bow-shaped element about said first pivot axis and second pivot axis, and wherein a safety switch-off is provided for said motor drive so that, by means of a measurement voltage induced in said instrument upon contact of said instrument with tissue inside the body, a measurement current flows which switches off said motor drives.

24. The device of claim 1, wherein a motor drive is provided for said first bow-shaped element and said second bow-shaped element in order to pivot said first bow-shaped element and said second bow-shaped element about said first pivot axis and second pivot axis, and further comprising a control unit for continuously determining the position of said instrument and for controlling said motor drive.

25. The device of claim 1, wherein means are provided for lifting said body surface into the space spanned by said first bow-shaped element and said second bow-shaped element.

* * * * *